(12) United States Patent
Lewandowski et al.

(10) Patent No.: US 6,604,436 B1
(45) Date of Patent: Aug. 12, 2003

(54) ULTRA-ACCELERATED NATURAL SUNLIGHT EXPOSURE TESTING FACILITIES

(75) Inventors: Allan A. Lewandowski, Evergreen, CO (US); Gary J. Jorgensen, Pine, CO (US)

(73) Assignee: Midwest Research Institute, Kansas City, MO (US)

(*) Notice: Subject to any disclaimer, the term of this patent is extended or adjusted under 35 U.S.C. 154(b) by 0 days.

(21) Appl. No.: 09/521,731

(22) Filed: Mar. 9, 2000

Related U.S. Application Data

(63) Continuation-in-part of application No. 09/006,746, filed on Jan. 13, 1998, now Pat. No. 6,073,500.

(51) Int. Cl.$^7$ ............................................. G01N 17/00
(52) U.S. Cl. .................. 73/865.6; 126/685; 359/1; 359/720; 359/726; 359/733; 359/742; 359/853; 374/57
(58) Field of Search .................. 73/865.6; 374/57; 359/853, 1, 720, 726, 727, 733–737, 742, 743; 126/573, 685, 692, 683, 684, 698

(56) References Cited

U.S. PATENT DOCUMENTS

| | | | | |
|---|---|---|---|---|
| 3,686,940 A | * | 8/1972 | Kockott ................. | 73/865.6 X |
| 3,886,791 A | * | 6/1975 | Grossman .............. | 73/865.6 X |
| 4,012,954 A | * | 3/1977 | Klippert ................. | 73/865.6 |
| 4,440,155 A | * | 4/1984 | Maloot et al. .......... | 126/698 X |
| 4,747,645 A | * | 5/1988 | Rudzki ................... | 356/51 |
| 4,807,247 A | * | 2/1989 | Robbins, III ........... | 73/865.6 X |
| 4,817,447 A | * | 4/1989 | Kashima et al. ........ | 73/865.6 |
| 5,069,942 A | * | 12/1991 | Anderson ............... | 427/387 |
| 5,153,780 A | * | 10/1992 | Jorgensen et al. ...... | 359/853 |
| 5,816,238 A | * | 10/1998 | Burns et al. ............ | 126/684 X |
| 6,015,950 A | * | 1/2000 | Converse ............... | 126/683 X |
| 6,225,551 B1 | * | 5/2001 | Lewandowski et al. .. | 136/246 |
| 6,302,100 B1 | * | 10/2001 | Vandenberg ............ | 126/698 |

FOREIGN PATENT DOCUMENTS

| | | | | |
|---|---|---|---|---|
| DE | 3430426 C1 | * | 10/1985 | ............ 422/53 |
| JP | 59-32847 | * | 2/1984 | ............ 374/57 |
| WO | WO 97/41417 | * | 11/1997 | ......... G01N/17/00 |
| WO | WO 00/07055 | * | 2/2000 | ......... G02B/17/00 |

* cited by examiner

Primary Examiner—Thomas P. Noland
(74) Attorney, Agent, or Firm—Paul J. White

(57) ABSTRACT

A multi-faceted concentrator apparatus for providing ultra-accelerated natural sunlight exposure testing for sample materials under controlled weathering conditions comprising: facets that receive incident natural sunlight, transmits VIS/NIR and reflects UV/VIS to deliver a uniform flux of UV/VIS onto a sample exposure plane located near a center of a facet array in chamber means that provide concurrent levels of temperature and/or relative humidity at high levels of up to 100× of natural sunlight that allow sample materials to be subjected to accelerated irradiance exposure factors for a significant period of time of about 3 to 10 days to provide a corresponding time of about at least a years worth representative weathering of sample materials.

18 Claims, 12 Drawing Sheets

ULTRA-ACCELERATED NATURAL SUNLIGHT EXPOSURE TESTING FACILITIES

The invention is a continuation-in-part of U.S. application Ser. No. 09/006,746 filed Jan. 13, 1998 now U.S. Pat. No. 6,073,500.

United States Government has rights in this invention pursuant to Contract No. DE-AC36-99GO10093 between the United States Department of Energy and the Midwest Research Institute.

BACKGROUND

1. Field of the Invention

The invention relates to a process for subjecting materials to accelerated irradiance exposure factors that permit about a year's worth of representative weathering to be accumulated in a period from about 3 to 10 days, under controlled weathering conditions that include several concurrent levels of temperature and/or relative humidity at very high levels of natural sunlight.

In the invention process, a solar concentrator [which may include a High Flux Solar Furnace (HFSF) and an Irradiance Redistribution Guide (IRG)] is used to obtain elevated levels (25–100×) of concentrated sunlight for accelerated testing of material samples. When an IRG is used, it provides the capability of being able to modify (redistribute) the Gaussian-shaped beam from the HFSF into a more uniform profile on a sample exposure plane.

Also encompassed in the invention process for obtaining ultra-accelerated natural sunlight exposure testing is the use of reflective apparatus such as multi-step and multi-faceted concentrators and refractive apparatus such as Fresnel lens concentrators, holographic concentrators, 2D or 3D micro lens arrays, and an array of Fresnel lens facets to obtain elevated levels (25–100×) of concentrated sunlight for accelerated natural sunlight testing of material samples.

By adequately controlling sample temperatures and demonstrating that reciprocity relationships are obeyed (i.e., the level of applied accelerated stresses does not change the failure/degradation mechanism), this novel capability allows materials to be subjected to accelerated irradiance exposure factors of 25–100×, thereby permitting a year's worth of representative weathering (in terms of natural sunlight exposure) to be accumulated in from about 3 to about 10 days.

2. Description of the Prior Art

U.S. Pat. No. 4,817,447 discloses a weathering chamber using lamps and sample temperature control using cooling air. Uniform sample irradiance at accelerated levels of up to 10 suns (within the UV bandwidth) appears attainable.

A test apparatus incorporating a mirror, which rejects infrared, is disclosed in U.S. Pat. No. 4,012,954. In the '954 patent, convective cooling air and a conductively cooled substrate are also incorporated. However, although convective cooling is used, the air movement is not used to deliver humidity to the samples during exposure; rather, humidity is provided by floating the sample substrate in a water bath. Further, as in the case of U.S. Pat. No. 4,817,477, the '954 patent uses artifical light sources for exposure of the samples.

U.S. Pat. No. 3,686,940 discloses a water-cooled cylindrical mirror, which rejects infrared radiation in an ultraviolet test apparatus. In the '940 patent, natural sunlight is not used.

A solar weathering device with control of sample temperature by cooling air is disclosed in U.S. Pat. No. 4,807,247. While this patent uses natural sunlight, a sample irradiance at accelerated levels of only up to 8 suns across the complete solar spectrum is employed.

U.S. Pat. No. 5,138,892 discloses accelerated light fastness testing of materials with xenon lamps and sample temperature control using airflow. Sample irradiance at accelerated UV levels of up to 8 suns (180 W/m$^2$ between 300–400 nm) are attainable. This patent does not utilize natural sunlight in its testing of materials.

A weather test machine using xenon lamps and sample temperature and humidity control using airflow is disclosed in U.S. Pat. No. 5,646,358. Uniform sample irradiance at accelerated levels up to 1–3 suns (within the UV bandwidth) is attainable. This patent does not utilize natural sunlight in its weather test machine.

U.S. Pat. No. 5,153,780 discloses a dish reflector and method for concentrating moderate solar flux uniformly on a target plane, said dish having stepped reflective surface characterized by a plurality of ring-like segments arranged about a common axis, each segment having a concave spherical configuration.

3. The Need for Capabilities Beyond the Prior Art

There is a need for devising facilities for ultra-accelerated natural sunlight exposure testing of materials and devices under controlled weathering conditions that include several concurrent levels of temperature and/or relative humidity at very high levels of natural sunlight. This need is associated with the desirability to be able to predict the in-service lifetimes of said materials and devices from correlation's derived between such realistically accelerated test results and those obtained during normal use conditions. Further, there is a need to conduct these ultra-accelerated exposure tests at irradiance exposure factors of from about 25 to 100 suns, wherein the irradiance is highly uniform. The need to conduct these ultra-accelerated natural sunlight exposure tests of materials and devices should exclude artificial light sources which invariably introduce uncertainties regarding realistic spectral content of the irradiance stress on samples being exposed. For example, the use of artificial light leads to unrealistic degradation mechanisms and failure modes of exposed materials caused by low wavelength (<300 nm) photons that are not present in terrestrial solar spectra.

SUMMARY OF THE INVENTION

In light of the drawbacks of the foregoing prior art, a general object of the present invention is to provide the unique capability to carry out ultra-accelerated exposure testing of materials and devices under controlled conditions that include several concurrent levels of temperature and/or relative humidity at very high levels of natural sunlight, thereby permitting about a year's worth of representative weathering, in terms of natural sunlight exposure, to be accumulated in from about 3 to about 10 days.

A further object of the present invention is to provide ultra accelerated exposure testing of materials and devices by controlling sample temperatures and humidities and demonstrating that reciprocity relationships are obeyed (i.e., level of applied accelerated stress does not change failure/degradation mechanism).

A yet further object of the present invention is to provide ultra-accelerated exposure testing of materials and devices that allows materials to be subjected to accelerated irradiance exposure factors of 25–100× to provide about a year's worth of representative weathering, in terms of natural sunlight exposure, to be accumulated in from about 3 to about 10 days.

A still further object of the invention is to provide a method of carrying out ultra-accelerated exposure testing of materials and devices utilizing a sample chamber that allows control of temperature and humidity during light exposure; wherein concentrated sunlight enters the chamber through an appropriate window, which may include quartz.

A further object yet still of the invention is to provide a method for carrying out ultra-accelerated exposure testing of materials and devices utilizing a cold mirror as a filter that reflects the ultraviolet/visible (UV/VIS) and transmits the near infrared (NIR) part of the solar spectrum, since the short wavelength (UV) light has been shown to be the predominant deleterious stress experienced by materials and devices during outdoor weathering.

Another object of the present invention is to provide a method of carrying out ultra-accelerated exposure testing of materials and devices under controlled weathering conditions, wherein conductive cooling of sample materials is provided by a water cooled substrate on to which samples are placed, and convective cooling is provided by blowing moist or dry air over the top surface of the samples, to provide high or low humidity to the samples during exposure of redirected concentrated sunlight into the exposure chamber to reduce the thermal load on the samples.

The invention is accomplished by the steps of: utilizing a solar concentrator to obtain elevated levels (25–100×) of concentrated sunlight with a uniform flux profile on the materials or samples being tested; splitting the solar spectrum into deleterious ultraviolet/visible (UV/VIS) light that enters the sample chamber; preventing concentrated near-infrared (NIR) radiation from entering the sample chamber to minimize undesirable thermal loading of material samples; and further control of temperature and/or relative humidity experienced by materials samples within the exposure chamber. The solar spectrum is split at a cut-off wavelength $\lambda_{cutoff}$ such that UV/VIS consists of wavelengths less than $\lambda_{cutoff}$ and VIS/NIR consists of wavelengths greater than $\lambda_{cutoff}$. Various combinations of concentrator designs (reflective and refractive), secondary reflectors, secondary concentrators, and turning mirrors can be used to provide the uniform flux. Additionally, the spectral splitting can be achieved at various points in the system through the use of coatings applied to any number of optical elements.

In terms of the best additional means for facilitating the general effect of ultra-accelerated natural sunlight exposure testing of materials, the facilities are as follows:

1) Multi-faceted concentrator design with facets having the following characteristics:

Facet centers located on a plane, parabola, sphere or other non-analytic shape;

Facet curvature that is flat, spherical, parabolic or aspheric; and

Facet reflector coatings designed to reflect UV light and transmit visible and IR, in the following configurations:
    a) Multi-faceted concentrator with geometry and design of facets to produce uniform flux on a sample chamber located at or near the aim point of the facets
    b) Multi-faceted concentrator with secondary reflector designed to deliver uniform flux to the sample chamber located near the center of the facet array
    c) Multi-faceted concentrator with secondary concentrator designed to deliver uniform flux to the sample chamber located near the exit of the secondary
    d) Multi-faceted concentrator with secondary reflector designed to deliver uniform flux to the sample chamber located below the secondary to allow a horizontal orientation of the sample chamber.
    e) Multi-faceted concentrator with secondary reflector designed to deliver uniform flux to the sample chamber located below a turning mirror-placed near the center of the facet array.
    f) Multi-faceted concentrator with secondary reflector designed to deliver uniform flux to the sample chamber below a turning mirror placed near the center of the facet array.

2) The multi-step concentrator of U.S. Pat. No. 5,153,780 Method and Apparatus for Uniformly Concentrating Solar Flux for PV Applications using a reflector coating designed to reflect UV light and transmit VIS and NIR in the following configurations:
    a) Multi-step concentrator with secondary reflector designed to deliver uniform flux to the sample chamber located near the center of the multi-step concentrator
    b) Multi-step concentrator with secondary concentrator designed to deliver uniform flux to the sample chamber located near the exit of the secondary
    c) Multi-step concentrator with secondary reflector designed to deliver uniform flux to the sample chamber located below the secondary to allow a horizontal orientation of the sample chamber,
    d) Multi-step concentrator with secondary reflector designed to deliver uniform flux to the sample chamber located below a turning mirror placed near the center of the multi-step concentrator
    e) Multi-step concentrator with secondary reflector designed to deliver uniform flux to the sample chamber below a turning mirror placed near the center of the multi-step concentrator 3) Fresnel lens concentrator/heat mirror configurations that only permit the desired spectral range to be transmitted:
    a) with heat mirror positioned above the top surface of the lens
    b) with one or both surfaces of the lens having a heat mirror coating
    c) with heat mirror positioned between the lens and the sample
    d) with heat mirror positioned between the lens and sample, but oriented as a relay mirror to reflect the desired wavelengths to a position perpendicular to the plane of the lens
    e) a two-stage Fresnel lens that interact as paired prisms to provide spectral selectivity
    f) any of the above configurations combined with a secondary concentrator to achieve the desired flux uniformity 4) Holographic concentrator in the following configurations:
    a) achieves both spectral splitting and uniform concentration in its fundamental design
    b) provides spectral splitting in its fundamental design and uses a secondary concentrator to achieve the uniform flux
    c) concentrates in its fundamental design and uses a secondary concentrator to achieve the uniform flux, but with a cold mirror coating on the secondary
    d) provides uniform flux in its fundamental design and uses a cold mirror to achieve the spectral splitting
    e) concentrates in its fundamental design and uses a secondary concentrator to achieve the uniform flux, but with a cold mirror placed between the lens and secondary to achieve the spectral splitting 5) Use of a 2D or 3D micro lens array to achieve flux uniformity and/or spectral splitting 6) An array of Fresnel lens facets can be used to achieve flux uniformity and in conjunction with a heat mirror or a cold mirror can provide spectral splitting

BRIEF DESCRIPTION OF THE DRAWINGS

The drawings that are incorporated in and form part of the specification will illustrate alternative embodiments of the invention, and serve together with the description to explain the principles of the invention wherein:

FIG. 29 shows the sample exposure chamber detail design that allows two levels of temperature and two levels of relative humidity to be maintained during sunlight exposure for the apparatus of the invention and ability to monitor spatial and spectral uniformity of the solar beam in situ during sample exposure; wherein:

PREFERRED MEANS FOR FACILITATING ULTRA-ACCELERATED NATURAL SUNLIGHT EXPOSURE TESTING

Figure 1:
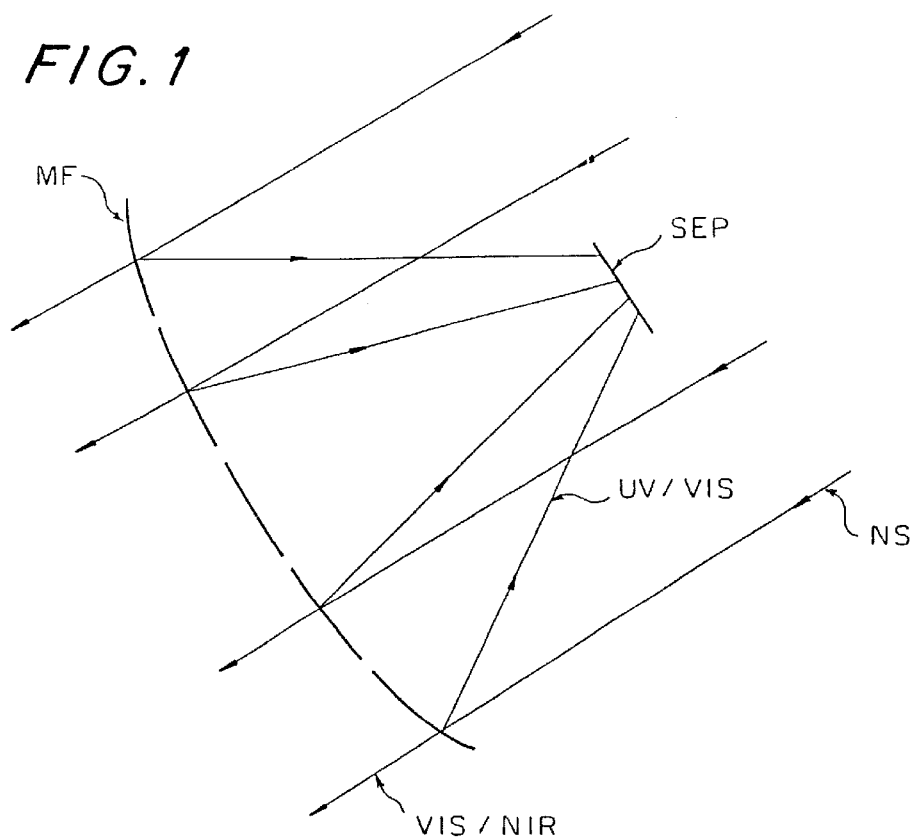
FIG. 1 shows a multi-faceted concentrator design that receives incident natural sunlight. The design transmits VIS/NIR and reflects UV/VIS onto a sample exposure plane.

Referring now to FIG. 1, there is shown a multi-faceted concentrator design MF that receives incident natural sunlight NS. The multi-faceted design transmits VIS/NIR and reflects UV/VIS onto a sample exposure plane SEP in chamber means (not shown) that provide single or multiple concurrent levels of temperature and/or relative humidity to facilitate accelerated aging.

Figure 2:
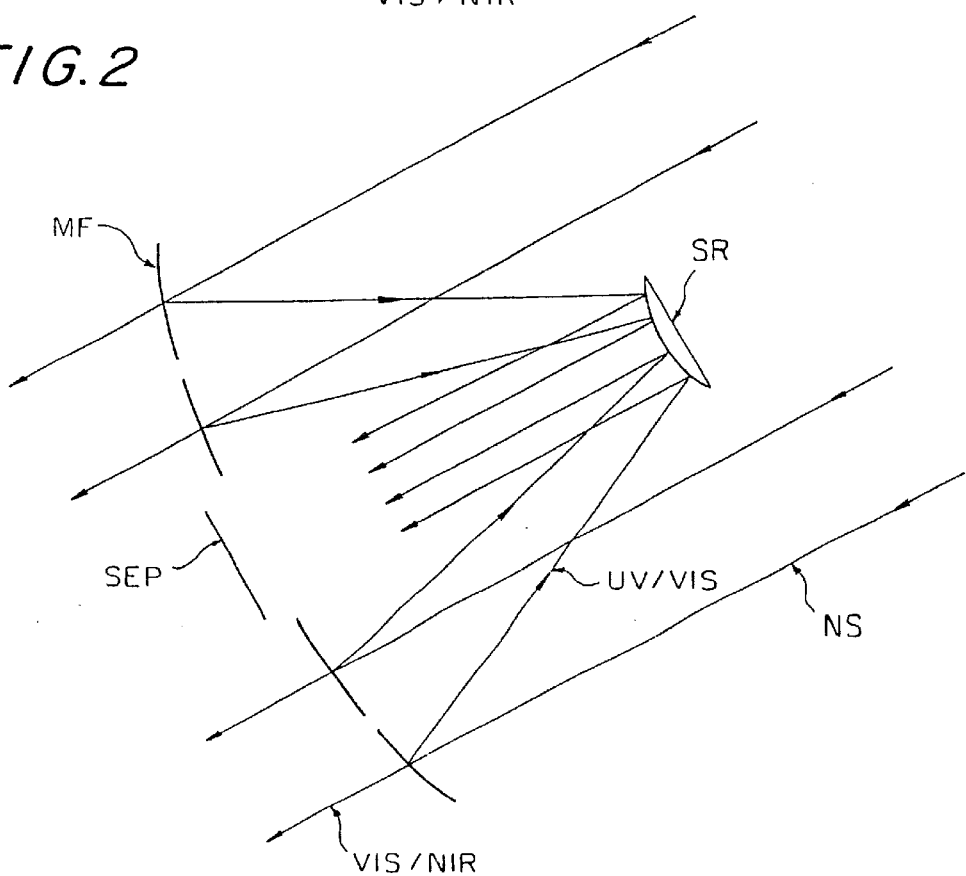
FIG. 2 shows a multi-faceted design that transmits VIS/NIR and reflects UV/VIS onto a secondary reflector, which in turn reflects uniformly concentrated natural sunlight onto a sample exposure plane.

Natural sunlight NS is made incident on yet another multi-faceted MF design as shown in FIG. 2. In this figure, the multi-faceted design transmits VIS/NIR and reflects UV/VIS onto a secondary reflector SR, which in turn reflects uniformly concentrated natural sunlight onto the sample exposure plane SEP located in chamber means that provide single or multiple concurrent levels of temperature and/or relative humidity to facilitate weathering of sample materials.

Figure 3:
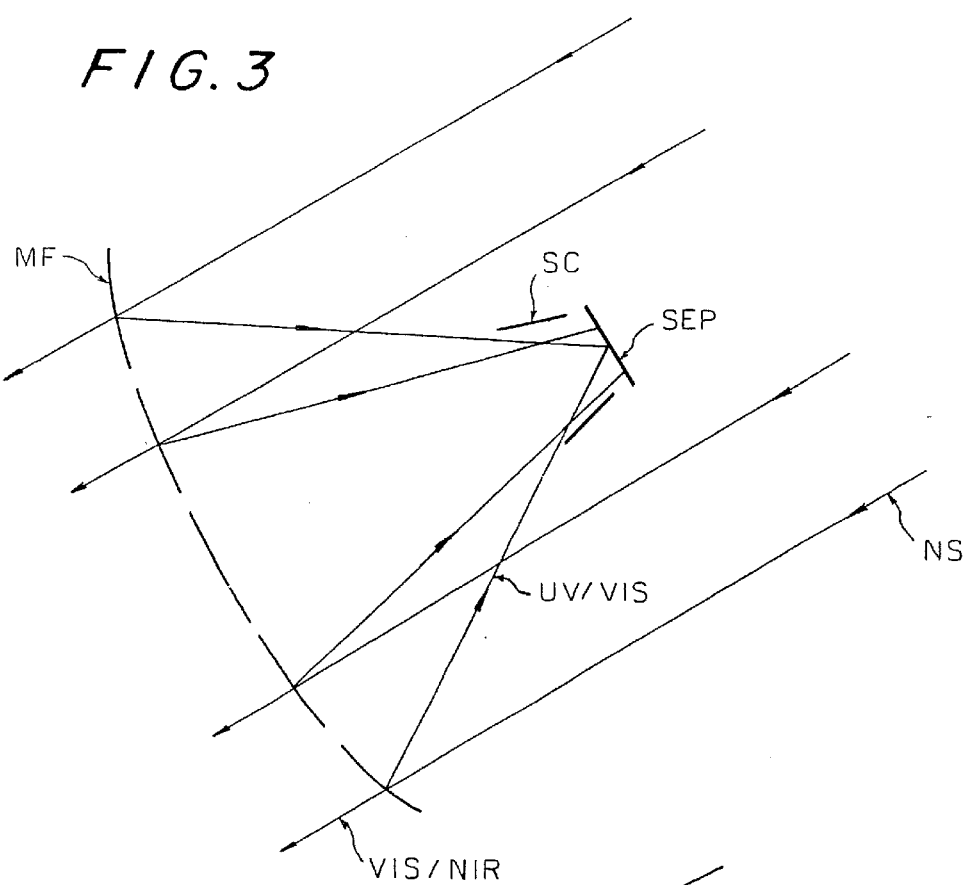
FIG. 3 shows a multi-faceted concentrator design for affecting ultra-accelerated natural sunlight exposure testing, in which natural sunlight is made incident upon a multi-faceted design that transmits VIS/NIR and reflects UV/VIS through a secondary concentrator and onto a sample exposure plane.

A multi-faceted concentrator design for affecting ultra-accelerated natural sunlight exposure testing is shown in FIG. 3 in which natural sunlight NS is made incident upon a multi-faceted design that transmits VIS/NIR and reflects UV/VIS through a secondary concentrator SC and onto a sample exposure plane SEP disposed within chamber means that provide single or multiple concurrent levels of temperature and/or relative humidity.

Figure 4:
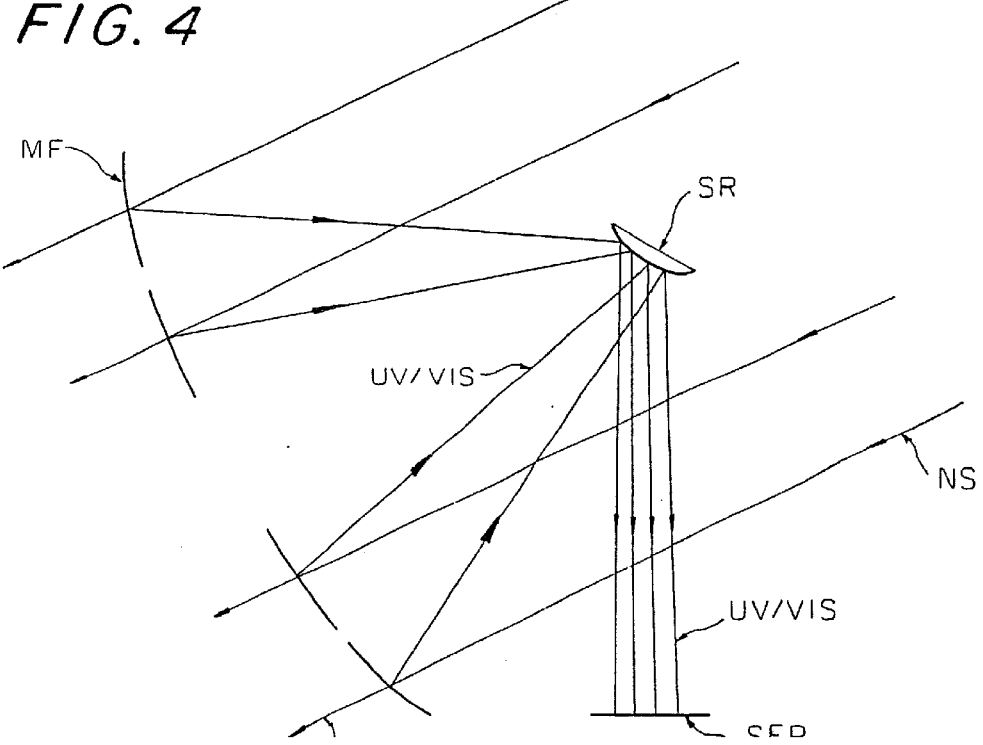
FIG. 4 shows a multi-faceted concentrator design with a secondary reflector that delivers uniform flux to a sample chamber located below the secondary reflector to allow a horizontal orientation of the sample chamber.

A multi-faceted concentrator MF design configuration with a secondary reflector SR designed to deliver uniform flux to a sample chamber located below the secondary reflector to allow a horizontal orientation of the sample chamber is shown in FIG. 4, in which natural sunlight NS is made incident upon the multi-faceted concentrator that transmits VIS/NIR and reflects UV/VIS onto the secondary reflector SR, which in turn, reflects a uniform flux of UV/VIS onto the horizontally disposed sample exposure plane SEP within chamber means that provide single or multiple concurrent levels of temperature and/or relative humidity.

Figure 5:
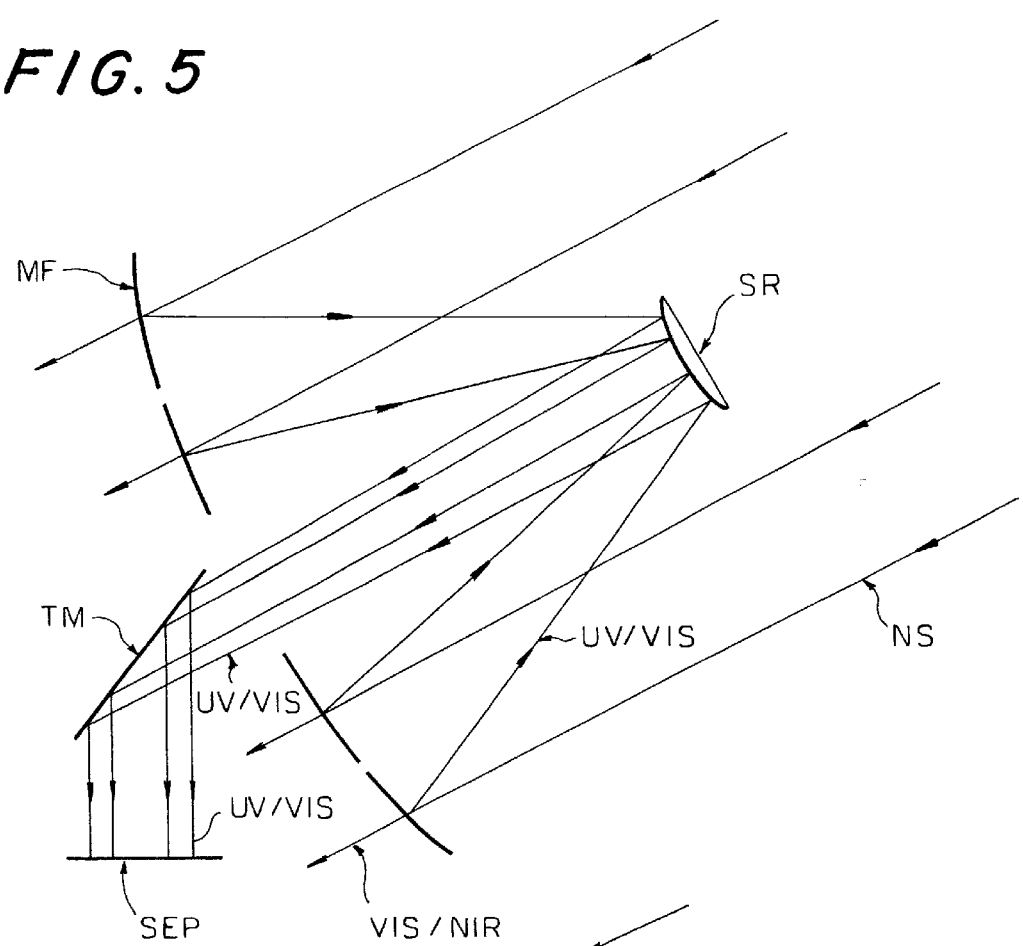
FIG. 5 shows a multi-faceted concentrator with a secondary reflector designed to deliver uniform flux to a sample exposure plane in a chamber located below a turning mirror.

A multi-faceted concentrator MF with a secondary reflector SR designed to deliver uniform flux to a sample exposure plane SEP in a chamber located below a turning mirror TM is shown in FIG. 5. In this figure, natural sunlight NS is made incident upon MF which transmits VIS/NIR and reflects UV/VIS onto secondary reflector SR which reflects a uniform flux onto a turning mirror TM, that in turn reflects UV/VIS onto a sample exposure plane SEP in chamber means that provide single or multiple concurrent levels of temperature and/or relative humidity to cause accelerated weathering.

Figure 6:
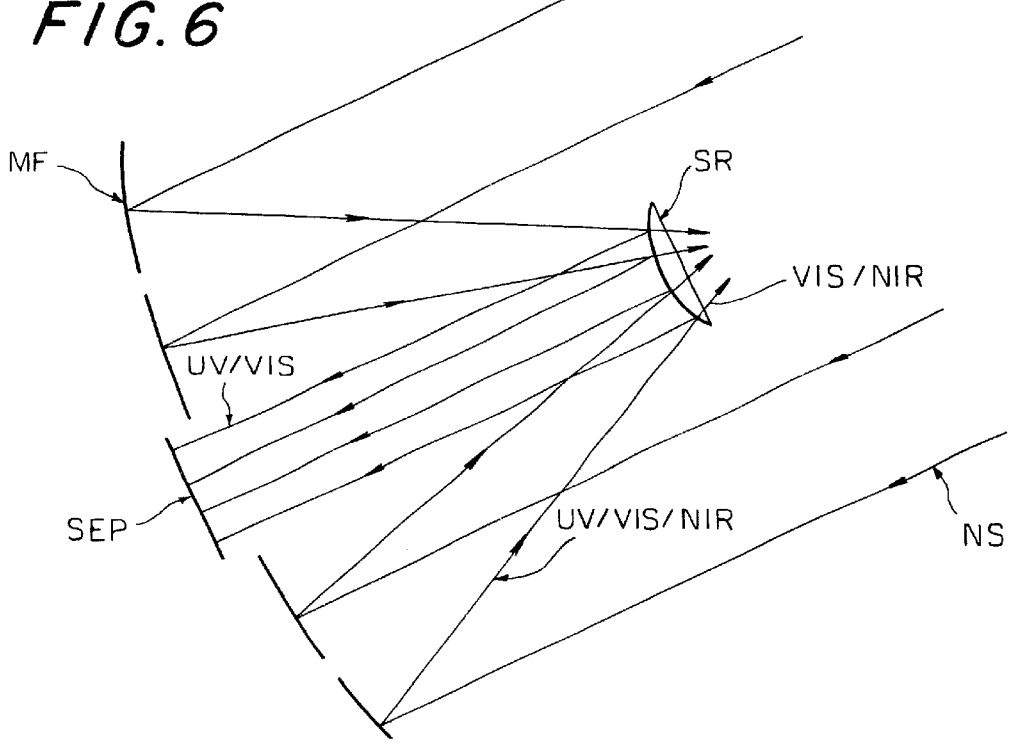
FIG. 6 shows a multi-faceted concentrator design that contains a reflector coating to reflect the full solar spectrum onto a secondary reflector that transmits VIS/NIR and reflects UV/VIS onto a sample exposure plane.

A multi-faceted concentrator MF that contains a reflector coating to reflect the full solar spectrum is shown in FIG. 6. In FIG. 6 natural sunlight is made incident upon the multi-faceted reflector coating, and the full spectrum UV/VIS/NIR is reflected onto a secondary reflector SR, which transmits VIS/NIR and reflects UV/VIS onto a sample exposure plane SEP located in chamber means that provide single or multiple concurrent levels of temperature and/or relative humidity to facilitate accelerated aging of the test samples.

Figure 7:
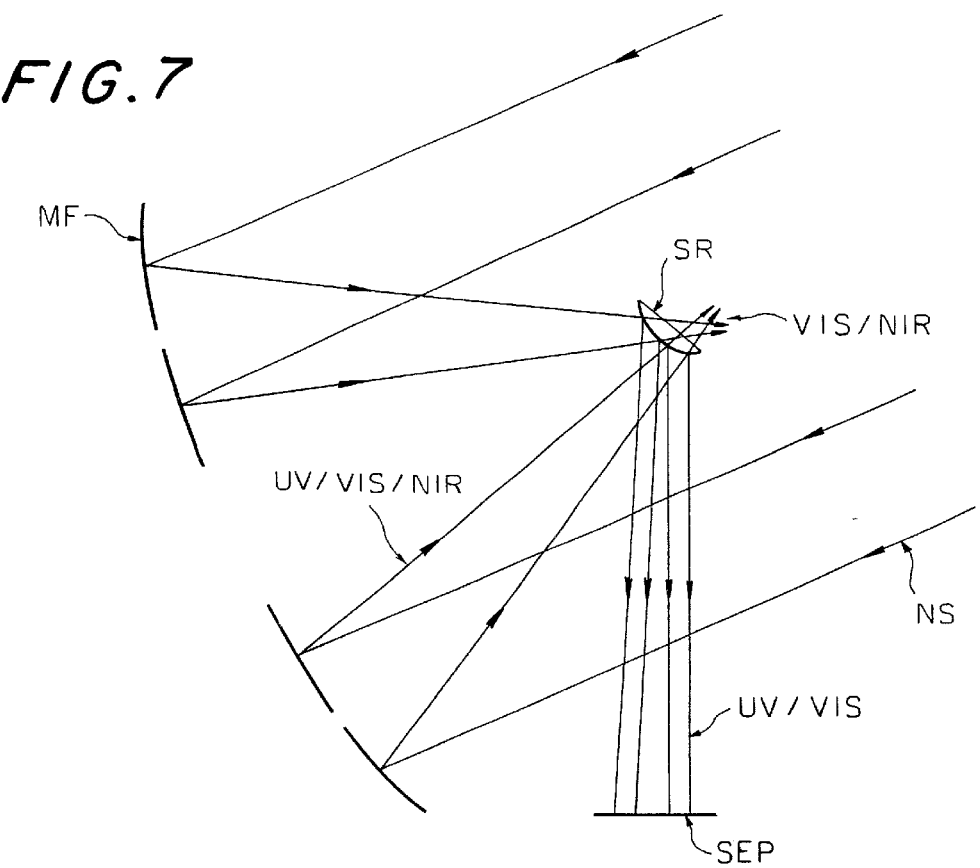
FIG. 7 shows a multi-faceted concentrator design that reflects the full solar spectrum onto a secondary reflector that in turn reflects only UV/VIS onto a horizontally disposed sample exposure plane.

A multi-faceted concentrator design MF that reflects the full solar spectrum onto a secondary reflector SR that in turn reflects only UV/VIS onto a horizontally disposed sample exposure plane SEP is shown in FIG. 7.

Figure 8:
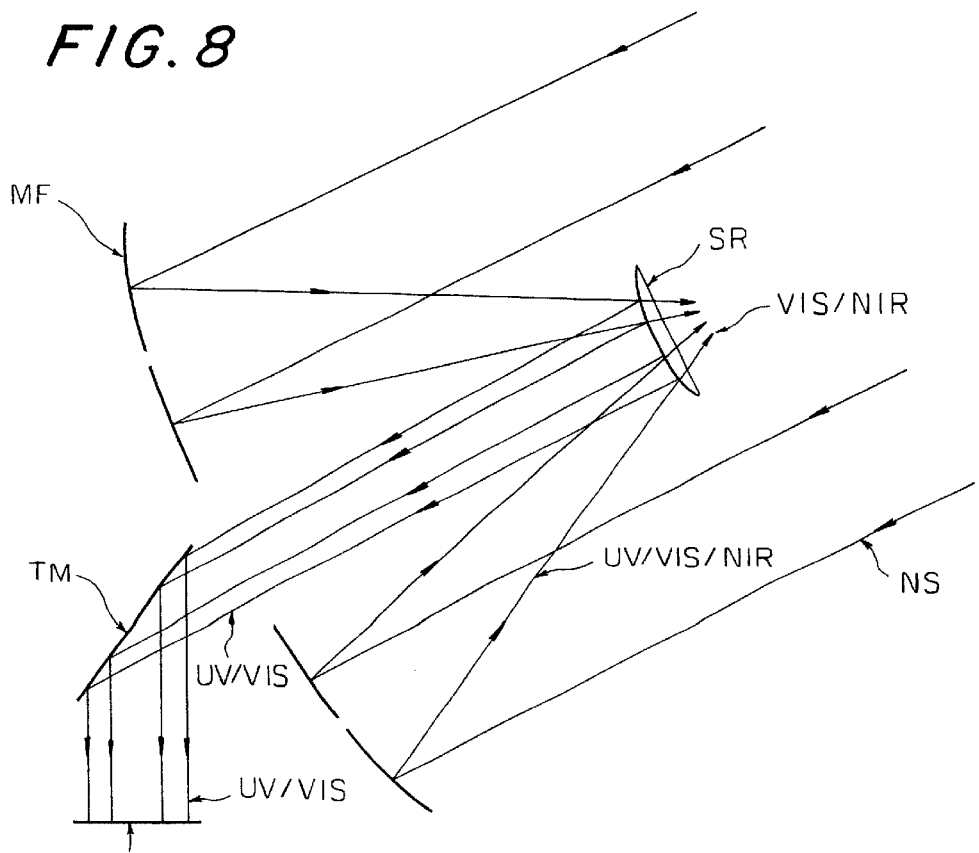
FIG. 8 shows a multi-faceted concentrator design that reflects the full solar spectrum UV/VIS/NIR. The full solar spectrum is reflected onto a secondary reflector that transmits VIS/NIR and reflects UV/VIS onto a turning mirror that reflects the UV/VIS onto a horizontally disposed sample exposure plane.

FIG. 8 shows a multi-faceted concentrator design MF that also reflects the full solar spectrum UV/VIS/NIR. The UV/VIS/NIR is reflected onto a secondary reflector SR which transmits VIS/NIR and reflects UV/VIS onto a turning mirror TM that reflects the UV/VIS onto a horizontally disposed sample exposure plane SEP located in chamber means that provides single or multiple concurrent levels of temperature and/or relative humidity to facilitate accelerated aging of sample materials.

Figure 9:
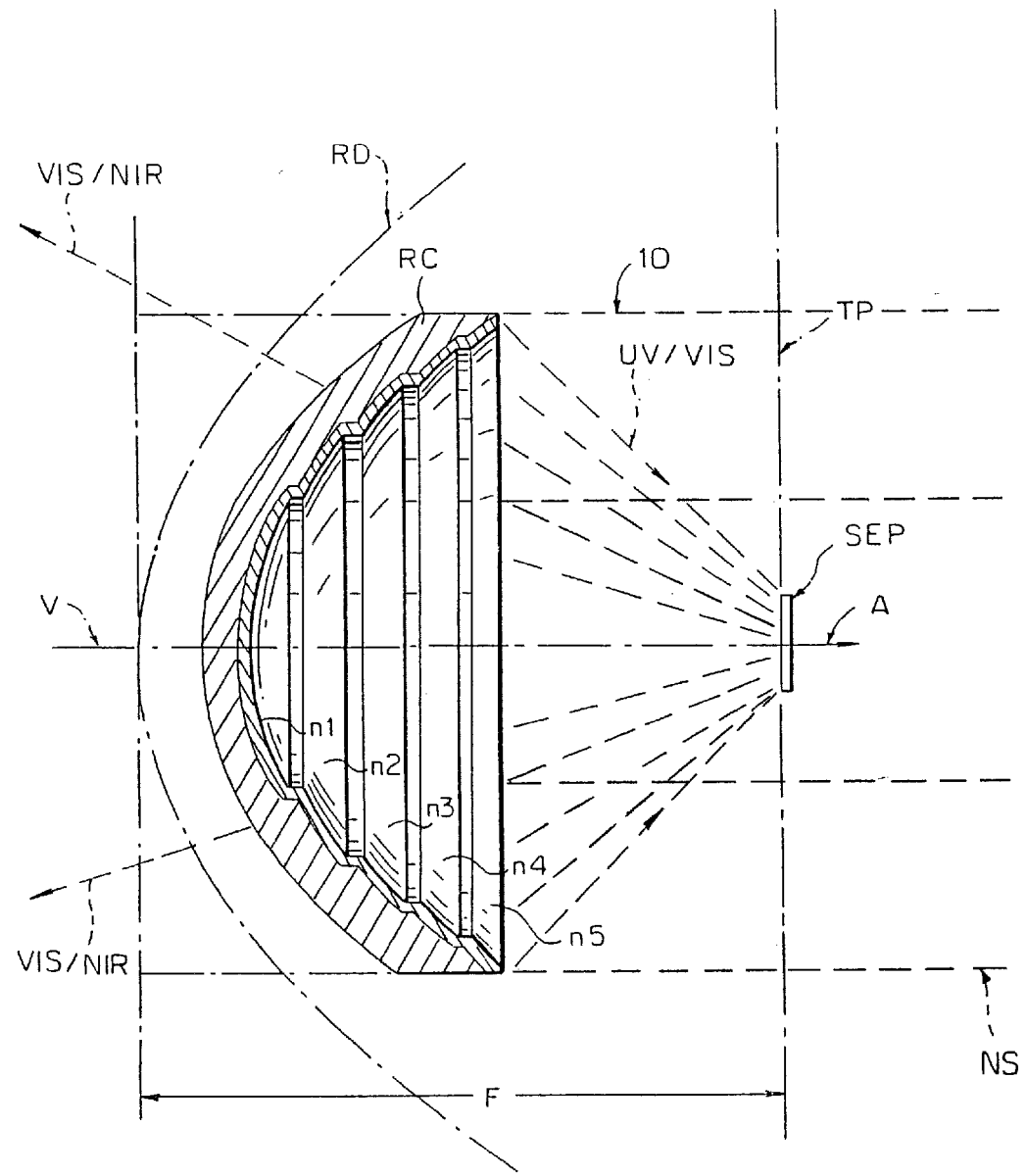
FIG. 9 shows a multi-stepped concentrator design for uniformly concentrating solar flux, in which a plural-stepped concentrator having reflective surfaces is used to reflect UV/VIS onto a sample exposure plane and transmit VIS/NIR. Other combinations of elements can be used with the multi-stepped concentrator including a secondary reflector or turning mirror to allow repositioning of the sample exposure chamber.

In FIG. 9, a multi-stepped concentrator design for uniformly concentrating solar flux is shown, in which a plural-stepped concentrator dish 10 having reflective surfaces comprised of, for example, 5 reflective surface elements, including a hub element designated by n1 and ring-shaped reflective elements n2–n5, lies symmetrically about a common axis A. The reflective elements n1–n5 are definable by reference dish RD, an imaginary parabolic dish that shares a common axis A, as shown. Reference dish RD has a focal length F and a target plane TP perpendicular to the A axis, at a distance equal to the focal length F from the vertex V, and the sample exposure plane SEP located in chamber means that provide single or multiple concurrent levels of temperature and/or relative humidity to facilitate accelerated aging. The multi-step concentrator employs a reflector coating RC that reflects UV/VIS onto the SEP and transmits VIS/NIR.

Alternative design configurations to the multi-step concentrator with geometry and design of facets to produce uniform flux on a sample chamber located at or near the aim point of the facets (as shown in FIG. 9), can be: a multi-step concentrator with secondary reflector designed to deliver uniform flux to the sample chamber located near the center of the facet array; a multi-step concentrator with secondary concentrator designed to deliver uniform flux to the sample chamber located near the exit of the secondary concentrator; a multi-step concentrator with secondary reflector designed to deliver uniform flux to the sample chamber located below the secondary concentrator to allow a horizontal orientation of the sample chamber; and a multi-step concentrator with secondary reflector designed to deliver uniform flux to the sample chamber below a turning mirror placed near the center near the facet array.

Figure 10:
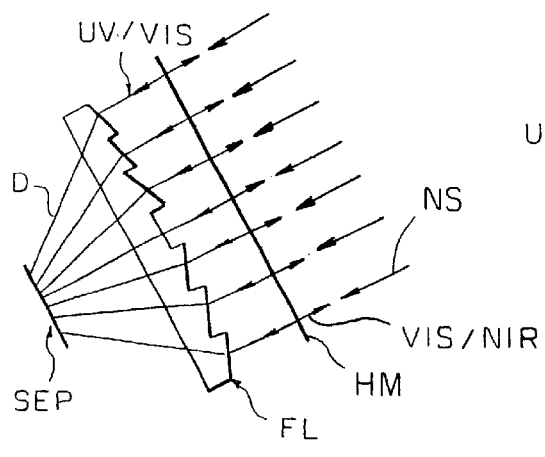
FIG. 10 shows a heat mirror positioned above the top surface of a Fresnel lens to allow only the desired spectral range to be transmitted and the Fresnel lens is used to uniformly concentrate the UV/VIS.

Referring now to FIG. 10, it can be seen that uniform, non-concentrated natural sunlight NS is incident on a heat mirror HM which reflects VIS/NIR but transmits UV/VIS. The UV/VIS is transmitted to a Fresnel lens FL to permit only the desired spectral range of uniform concentrated spectrally split natural sunlight D to be incident upon the sample exposure plane SEP.

Figure 11:
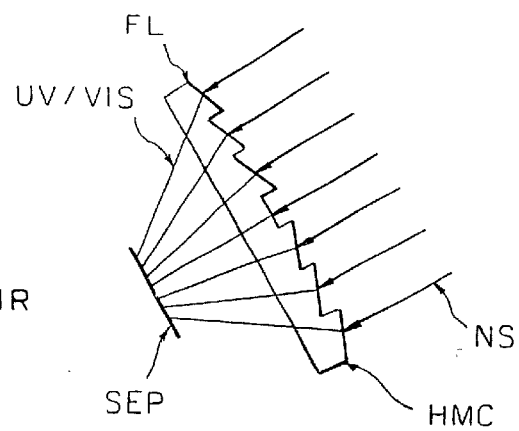
FIG. 11 shows another use of the Fresnel lens in which one or both surfaces of the Fresnel lens has a heat mirror coating that allows only the desired spectral range to be transmitted and the Fresnel lens is used to uniformly concentrates the UV/VIS.

One or both of the surfaces of a Fresnel lens may be provided with a heat mirror coating HMC that allows the desired spectral range to be transmitted, as is shown in FIG. 11, where uniform, non-concentrated incident natural sunlight NS is made incident upon a heat mirror coating HMC on either the top or bottom or both sides of a Fresnel lens FL, so that UV/VIS is transmitted onto a sample exposure plane SEP.

Figure 12:
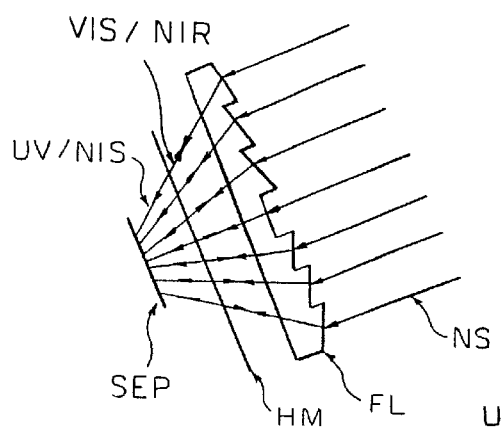
FIG. 12 shows a Fresnel lens in which a heat mirror is positioned between the Fresnel lens and the sample plane to allow only the spectral range to be transmitted and the Fresnel lens is used to uniformly concentrate the UV/VIS.

Another of the preferred embodiments for facilitating ultra-accelerated natural sunlight exposure testing is by a heat mirror HM positioned between a Fresnel lens and the sample plane to permit only the desired spectral range to be transmitted, as is shown in FIG. 12. In FIG. 12, uniform, non-concentrated incident natural sunlight NS is made incident to a Fresnel lens FL which transmits a uniformly-concentrated, broad-band spectral range to a heat mirror HM that reflects VIS/NIR, but transmits UV/VIS onto a sample exposure plane SEP.

Figure 13:
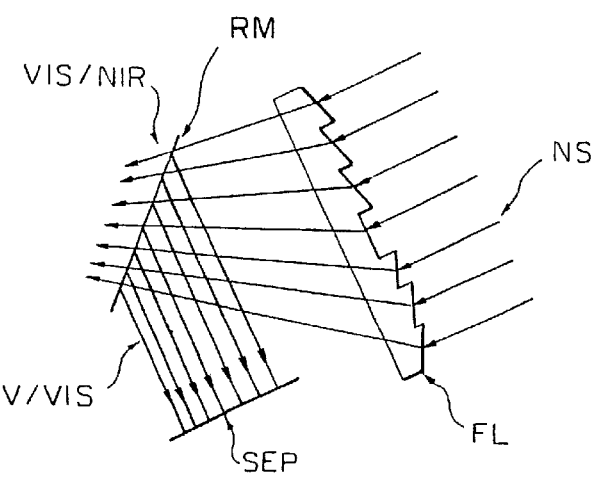
FIG. 13 shows a Fresnel lens that provides uniform concentrated light on a sample exposure plane that is perpendicular to the plane of the Fresnel lens and uses a relay mirror that performs the desired spectral splitting and is positioned at an appropriate angle to achieve uniformity.

In a further preferred embodiment, as shown in FIG. 13, a Fresnel lens FL is designed to provide uniform non-concentrated incident sunlight NS and transmits the full spectral range onto a relay mirror RM, which in turn transmits VIS/NIR and reflects UV/VIS onto sample exposure plane SEP.

Figure 14:
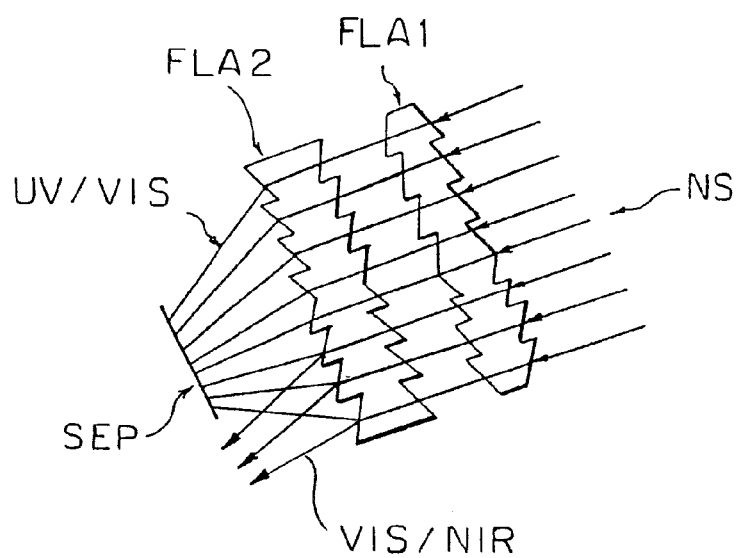
FIG. 14 shows a two-stage (double-layer) Fresnel lens arrangement in which the surface geometry is such that the desired concentrated uniformity over the required area in the sample exposure plane is achieved but the surface features of the two arrays (separated by low-index of refraction media such as air with n=1) interact as paired prism elements to provide spectral selectivity.

In the preferred embodiment of FIG. 14, a 2-stage or double layer uniform concentrated UV/VIS Fresnel lens arrangement is used in which the surface geometry is such that not only is the desired concentrated uniformity over the required area in the sample exposure plane achieved but the surface features of the arrays (separated by a low-index of refraction media, such as air with n=1) interacts as paired prism elements to provide spectral selectivity. In FIG. 14, uniform non-concentrated natural sunlight NS is made incident to a first Fresnel/prism array FLA 1 so that the light is spatially separated into distinct wavelengths ("rainbow"). A masking pattern is then placed on to the top surface of a second Fresnel prism array FLA 2 to block unwanted wavelengths>$\lambda_{cutoff}$ (i.e. high VIS and NIR) such that the light exiting FLA 2 is recombined light with a $\lambda<\lambda_{cutoff}$ prior to directing the re-combined light with the $\lambda<\lambda_{cutoff}$ onto a sample exposure plane SEP.

Figure 15:
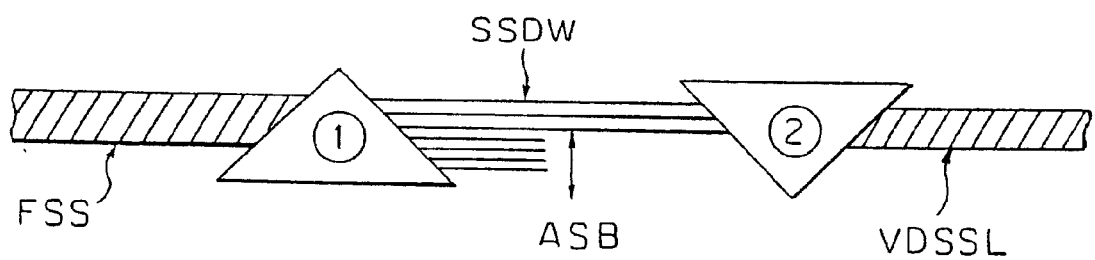
FIG. 15 shows a refractive means by which the spatial splitting of wavelengths can be accomplished by using a pair of dispersion prisms to achieve spectral selectivity.

A pair of dispersion prisms (1 and 2) can be used to achieve spectral selectivity in the following manner, as shown by FIG. 15, in which there is first made an input of uniform distribution of the full solar spectrum FSS through a first prism to affect spatially separated/distinct wavelengths SSDW on the one hand and to cause adjustable stop blocks of transmitted wavelengths $\lambda>\lambda_{UV/VIS}$ or $\lambda>\lambda_{cutoff}$, and in which prism No. 2 is used to reconstruct or homogenize the spatially selected wavelengths from prism No. 1 to obtain an output uniform distribution of spectrally selected light UDSSL with $\lambda<\lambda_{cutoff}$, which is then concentrated in a Fresnel lens-lens-like manner. In this connection, it should be noted that the adjustable stop blocks can be directly applied to the first surface of prism No. 2 (as for example by the use of black paint).

Figure 16:
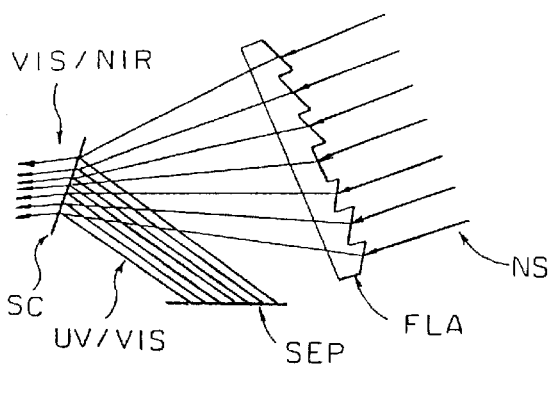
FIG. 16 takes any of the configurations described in FIGS. 10 to 14 above in which a secondary concentrator is incorporated to achieve the desired flux uniformity and/or to reposition the sample exposure plane to a more desirable orientation (e.g., horizontal) during exposure testing (where the secondary concentrator may also be used to perform spectral selectivity, as for example, functioning also as a cold mirror).

In general, any of the configurations described in FIGS. 10–14, in which a secondary concentrator is incorporated to achieve the desired flux uniformity and/or to reposition the sample exposure plane to a more desirable orientation (e.g., horizontal) during exposure testing may be suitable and it should be noted that the secondary concentrator may also be used to perform the spectral selectivity, for example, so as to be able to function as a cold mirror as is shown in FIG. 16. In FIG. 16, uniform, non-concentrated natural sunlight NS is made incident upon a tracking primary Fresnel lens array FLA, and from which the transmissions are adjusted with a secondary concentrator SC that adjusts with primary tracking. The secondary concentrator transmits VIS/NIR (as is done with a cold mirror) where upon uniform concentrated UV/VIS is then reflected onto a fixed horizontal sample exposure plane SEP.

Figure 17:
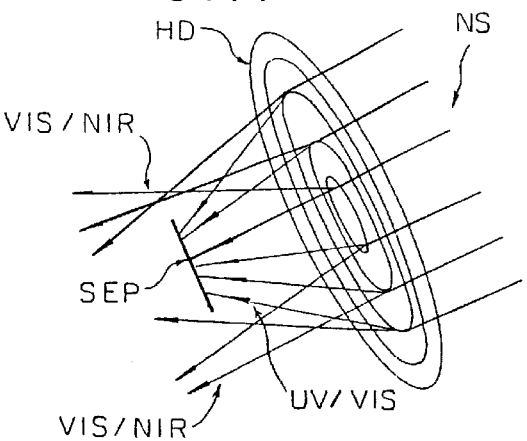
FIG. 17 shows a holographic device that concentrates the solar irradiance and performs the desired spectral splitting and provides flux uniformity over the required area in a sample exposure plane (SEP).

The specific embodiment of FIG. 17 shows a holographic device that concentrates the solar irradiance and performs the desired spectral splitting and provides flux uniformity over the required area in a sample exposure plane. More specifically, in FIG. 17, uniform, non-concentrated natural sunlight NS is made incident upon a holographic device HD which directs concentrated UV/VIS onto a sample exposure plane SEP, and the spectrally split VIS/NIR is made to miss the sample exposure plane.

Figure 18:
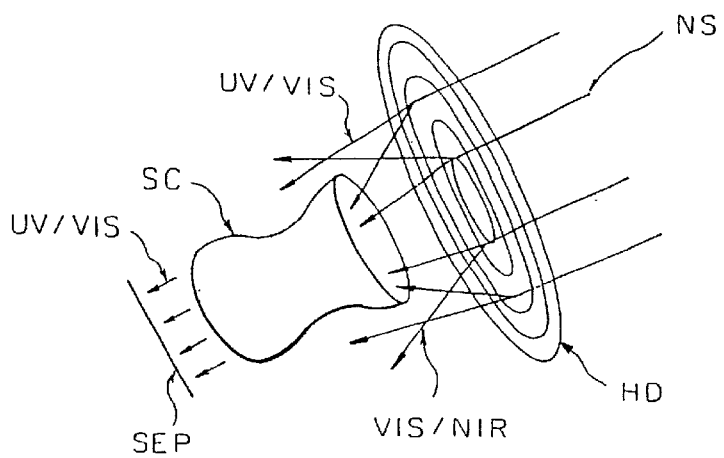
FIG. 18 shows a holographic device that concentrates the solar irradiance and performs the desired spectral splitting and uses a secondary concentrator to provide flux uniformity over the required area in a sample exposure plane (SEP).

In the preferred embodiment of FIG. 18, there is shown a holographic device that concentrates the solar irradiance and performs the desired spectral splitting and uses a secondary concentrator to provide flux uniformity over the required area in the sample exposure plane. More specifically, in FIG. 18, uniform non-concentrated natural sunlight NS is made incident upon a holographic device HD, which spectrally splits the incident light into a non-uniform concentrated UV/VIS input so that it falls on a secondary concentrator SC to provide a uniform concentrated UV/VIS output on the sample exposure plane SEP, and whereby the non-uniform concentrated VIS/NIR is split away from the secondary concentrator.

Figure 19:
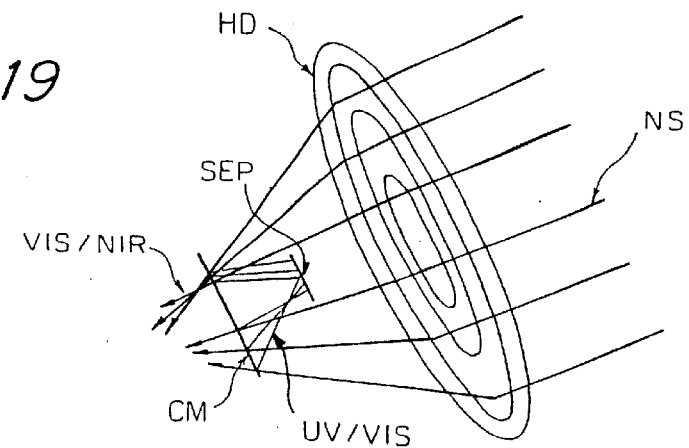
FIG. 19 shows a holographic device that concentrates the solar irradiance and provides flux uniformity over the required area in a sample exposure plane, and uses a cold mirror to achieve the desired spectral splitting.

In yet another preferred embodiment, as shown in FIG. 19, a holographic device HD is used to direct uniform, non-concentrated natural sunlight NS, where upon the incident NS is directed through the HD to transmit VIS/NIR onto a cold mirror CM that reflects UV/VIS onto a sample exposure plane SEP.

Figure 20:
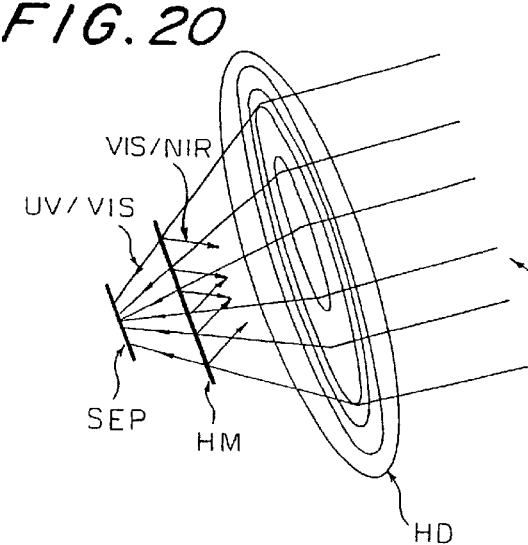
FIG. 20 shows a holographic device that concentrates the solar irradiance and provides flux uniformity over the required area in a sample exposure plane, and uses a heat mirror to achieve the desired spectral splitting.

A still further embodiment of the invention as is shown in FIG. 20, which utilizes a holographic device that concentrates the solar irradiance and provides flux uniformity over the required area in a sample exposure plane and utilizes a heat mirror to achieve the desired spectral splitting (UV+low–VIS versus high–VIS+NIR). In particular, the holographic device HD is utilized to direct uniform, non-concentrated natural sunlight NS through a heat mirror HM to effect spectral splitting so that, UV/VIS is transmitted onto a sample exposure plane SEP and the VIS/NIR is reflected off of the heat mirror.

Figure 21:
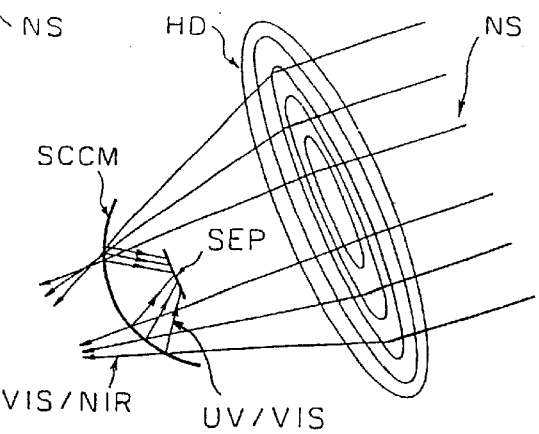
FIG. 21 shows a holographic device that concentrates the solar irradiance and uses a secondary concentrator to provide flux uniformity over the required area in a sample exposure plane and also uses the secondary concentrator to achieve the desired spectral splitting.

A holographic device HD through which uniform, non-concentrated natural sunlight NS is directed is shown in FIG. 21. In the preferred embodiment of FIG. 21, the holographic device directs the incident NS so that transmitted VIS/NIR is passed through a secondary concentrator cold mirror SCCM and UV/VIS is reflected from the SCCM onto a sample exposure plane SEP.

Figure 22:
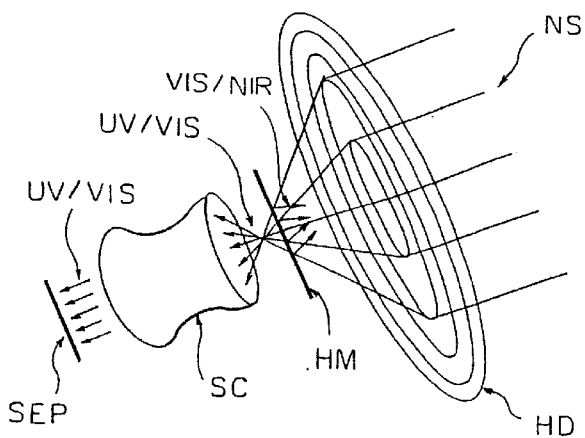
FIG. 22 shows a holographic device that concentrates the solar irradiance and uses a secondary concentrator to provide flux uniformity over the required area in a sample exposure plane and uses a heat mirror to achieve the desired spectral splitting.
Figure 23:
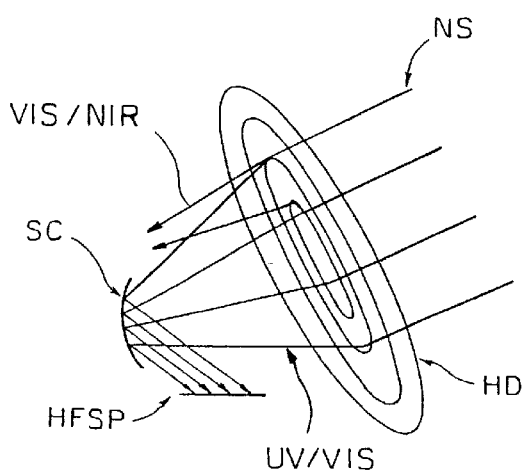
FIG. 23 utilizes any of the configurations described in FIGS. 17–22 above, in which a secondary concentrator is incorporated to achieve the desired flux uniformity and/or to reposition the sample exposure plane to a more desirable orientation (e.g., horizontal) during exposure testing.

In the specific embodiment shown in FIG. 22, a holographic device HD is utilized to direct uniform, non-concentrated natural sunlight NS onto a heat mirror HM that transmits concentrated non-uniform UV/VIS flux onto a secondary concentrator SC, which concentrates uniform UV/VIS flux onto a sample exposure plane SEP, while the heat mirror simultaneously reflects VIS/NIR. Any of the facilities shown in the configurations of FIGS. 17–22, in which a secondary concentrator SC is incorporated to achieve the desired flux uniformity and/or reposition the sample exposure plane to a more desirable orientation (for example, horizontal) during operation can be used by adjusting the secondary concentrator with primary tracking, as is shown in the specific embodiment of FIG. 23. In FIG. 23, uniform non-concentrated natural sunlight NS is directed through a holographic device HD so that the UV/VIS portion of the NS is reflected off of a secondary concentrator SC (and the VIS/NIR portion is transmitted) that is adjusted with primary tracking so as to reflect uniformly concentrated natural sunlight onto a horizontal fixed sample plane HFSP. VIS/NIR is transmitted by the SC.

Figure 24A:
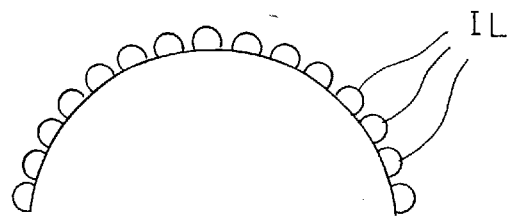
FIG. 24 shows as a means for refractively achieving concentrated solar irradiance and/or spectral splitting and/or flux uniformity with a 2-dimensional or 3-dimensional array of micro-lenses.
Figure 24B:
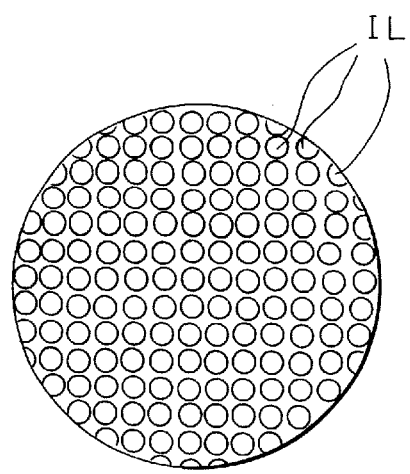

Another means for refractively achieving concentrated solar irradiance and/or spectral splitting and/or flux uniformity is with a 2-dimensional or 3-dimensional array of micro lenses. In this connection, reference is made to FIG. 24 in which such an array of micro lenses is shown in cross section. As can be seen in FIG. 24, a cross sections view of the 2-dimensional or 3-dimensional array of micro lenses in which the individual lenses IL is shown. A top view of the individual micro lenses is also shown.

Figure 25:
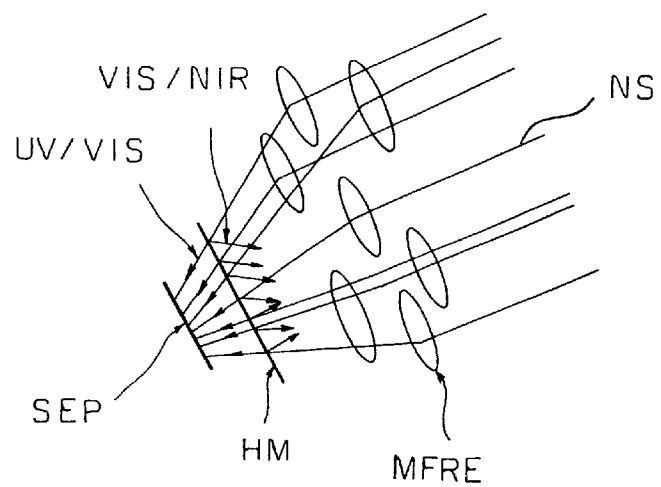
FIG. 25 shows a multi-faceted refractive element MFRE (i.e., lenses or Fresnel lenses) used in conjunction with a heat mirror.

Just as multi-faceted reflective elements can be used to achieve uniform concentration, multi-faceted refractive elements (i.e., lenses or Fresnel lenses) can be used in conjunction with heat mirrors and/or cold mirrors and/or secondary concentrators, as is shown in FIG. 25. In FIG. 25, uniform, non-concentrated natural sunlight NS is directed through a multi-faceted array of lenses MFRE onto a heat mirror HM which transmits UV/VIS onto a sample exposure plane SEP and reflects VIS/NIR. This multi-faceted array of lenses may also be substituted for holographic devices shown in the embodiments of FIGS. 17–23, where heat and/or cold mirror coatings are applied to the lenses or separate elements or are incorporated into secondary concentrators.

Figure 26:
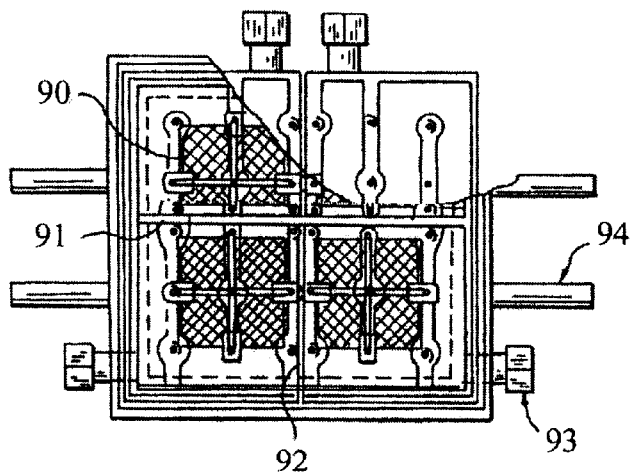
FIG. 26 shows a cut-away view of an advanced exposure chamber design in accordance with the invention.

FIG. 26 is a top view of an alternative embodiment of the exposure chamber design, showing a cut-away view. Samples 90 are disposed so that they are separated by a chamber divider 91. The chamber divider is in turn separated by an insulation divider 92. In this embodiment, larger heating/cooling ports 93 are disposed below the humidity ports 94.

Figure 27:
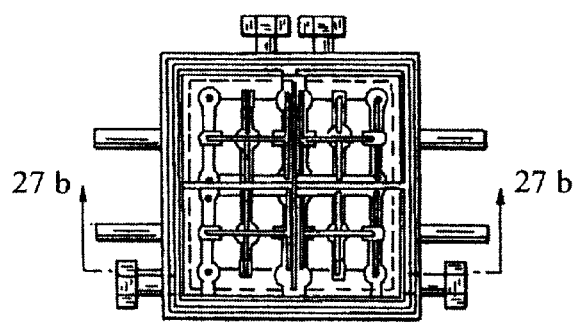
FIGS. 27a, 27b and 27c show additional views of the embodiment of the exposure chamber design of FIG. 26.
Figure 27:
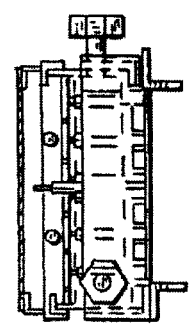
Figure 27:
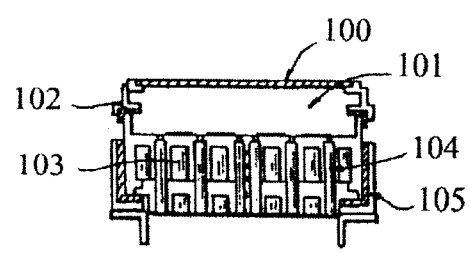

As can be seen from the embodiment in FIG. 27, a number of alternative ways exist for improving the performance and ease of use of the sample exposure chamber. For example, baffles may be added with heating and cooling using a circulating bath with an approximate range of –20 to 100° C., thereby eliminating the need for individual electric cartridge heaters that give rise to non-uniform sample exposure temperatures within a given quadrant. The baffles and chambers may be machined out of one solid block of aluminum and enlarged slightly. This would allow more room for thermocouple wires and insulation and also provide a better seal between chambers. In addition, and insulated, outside shell may be fabricated, that both chambers would rest in. This design configuration helps keep temperatures constant and makes the assembly solid.

FIG. 27a is a top view of FIG. 26 minus the samples. FIG. 27b is a view taken along the line 27b—27b of FIG. 27a, showing the quartz cover plate 100, humidity chamber 101, the insulation 102, a heating/cooling chamber with baffles 103, fiber optic guides 104, and insulated box 105, around the chambers.

Figure 28:
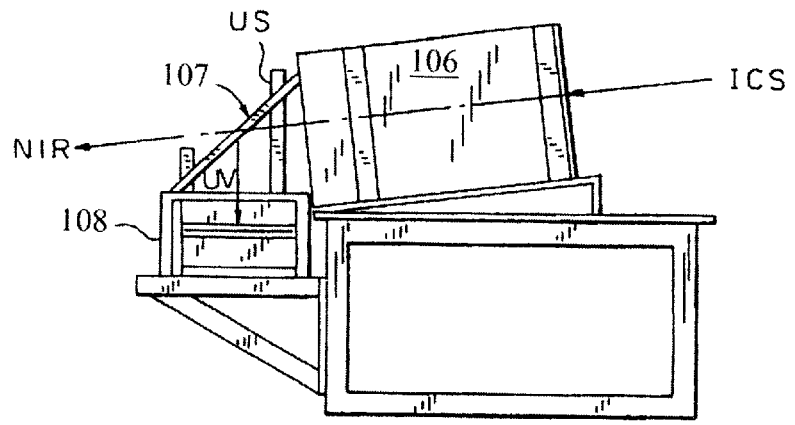
FIG. 28 is a perspective view of the system layout of the apparatus of the invention showing the sample chamber interface, via a cold mirror, with the HFSF/IRG components.
Figure 29A:
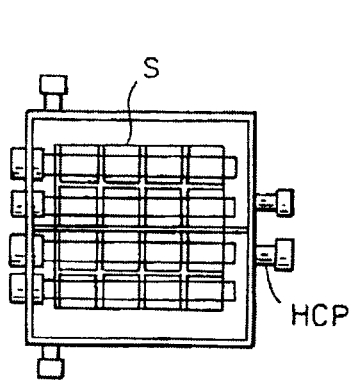
FIG. 29a shows a top view of the heating/cooling chamber with samples in place.
Figure 29B:
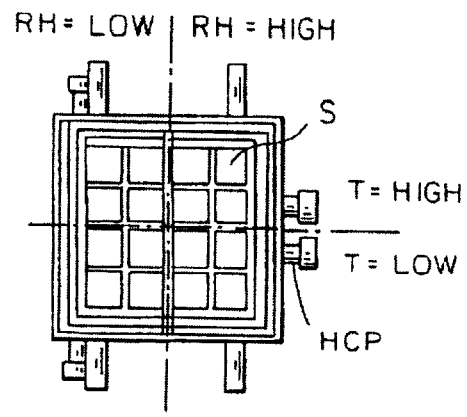
FIG. 29b shows a top view of the chamber with humidity chamber in place.
Figure 29C:
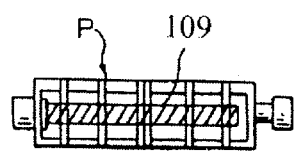
FIG. 29c is a side view of the heating/cooling chamber.
Figure 29D:
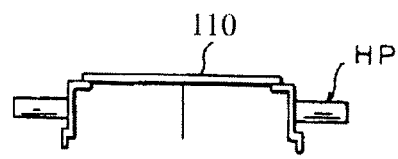
FIG. 29d is a side view of the humidity chamber.

FIG. 28 shows the cross-sectional system layout of the IRG 106, cold mirror 107 and sample chamber 108, wherein incident concentrated sunlight ICS is passed through the IRG and uniform sunlight US exits. An improved chamber was designed and fabricated that allows up to four replicate samples of about 2.2 cm×0.2.2 cm square in size each to be exposed to the same high level of accelerated solar flux at two levels each of temperature and humidity. For example, at a given flux (e.g., 50×suns), sets of samples can be simultaneously exposed at Tlow, RHlow, Tlow, Rhhigh; Thigh, RHlow; and Thigh, RH high. This allows a four-fold increase in experimental throughput at a particular exposure flux.

A detailed drawing of the sample exposure chamber is shown in FIG. 29. FIG. 29a is a top view of the heating/cooling chamber with samples S in place, and showing heating/cooling parts HCP. FIG. 29b is a top view of the chamber with the humidity chamber in place. During testing the samples are mechanically attached to the top surface of the heating/cooling chamber to provide good thermal contact. The humidity chamber sits atop the heating/cooling chamber. FIG. 29c is a side view of the heating/cooling chamber, showing the pathway P for fiber optic probes and the cross section view of the heaters 109. FIG. 29d is a side view of the humidity chamber showing the humidity ports HP and the highly transmissive quartz window 110.

We claim:

1. In a multi-faceted concentrator apparatus for providing ultra-accelerated natural sunlight exposure testing for sample materials under controlled weathering conditions comprising means for concentrating solar flux uniformly as concentrated uniform reflected light and means for directing said concentrated uniform reflected light onto sample materials contained in a chamber having means to provide single or multiple concurrent levels of temperature and/or relative humidity, wherein said means for concentrating solar flux uniformly and means for directing concentrated uniform reflected light comprise: a multi-faceted concentrator comprising facets that receive incident natural sunlight, transmits VIS/NIR and reflects a uniform flux of UV/VIS onto a sample exposure plane located at or near aim points of said facets in chamber means that provide concurrent levels of temperature and/or relative humidity at high levels of up to 100× of natural sunlight that allow sample materials to be subjected to accelerated irradiance exposure factors for a significant period of time of about 3 to 10 days to provide a corresponding time of about at least a years worth of representative weathering of sample materials.

2. The apparatus of claim 1 wherein said multi-faceted concentrator comprises: facets that receive incident natural sunlight, transmits VIS/NIR and reflects UV/VIS onto a secondary reflector that delivers a uniform flux of UV/VIS onto the sample exposure plane, said sample exposure plane located near a center of a facet array in the chamber means that provide concurrent levels of temperature and/or relative humidity that allow sample materials to be subjected to accelerated irradiance exposure factors for a significant period of time of about 3 to 10 days to provide a corresponding time of about at least a years worth representative weathering of sample materials.

3. The apparatus of claim 1 wherein said multi-faceted concentrator comprises: facets that receive incident natural sunlight, transmits VIS/NIR and reflects a uniform flux of UV/VIS through a secondary concentrator and onto the sample exposure plane, said sample exposure plane located near an exit of the secondary concentrator in the chamber means that provide concurrent levels of temperature and/or relative humidity that allow sample materials to be subjected to accelerated irradiance exposure factors for a significant period of about 3 to 10 days to provide a corresponding time of about at least a years worth of representative weathering of sample materials.

4. The apparatus of claim 1 wherein said multi-faceted concentrator comprises: facets that receive incident natural sunlight, transmits VIS/NIR and reflects UV/VIS onto a secondary concentrator which delivers a uniform flux of UV/VIS onto the sample exposure plane, said sample exposure plane located below said secondary reflector to allow a horizontal orientation of the sample chamber means in which the sample exposure plane is disposed.

5. The apparatus of claim 1 wherein said multi-faceted concentrator comprises: a facet array that receives incident natural sunlight, transmits VIS/NIR and reflects UV/VIS onto a secondary reflector that reflects a uniform flux of UV/VIS onto a turning mirror located near a center of the facet array; said turning mirror being disposed to reflect said uniform flux of UV/VIS onto the sample exposure plane, said sample exposure plane located in the chamber means below said turning mirror.

6. The apparatus of claim 1 wherein said multi-faceted concentrator array comprises: facets that receive incident natural sunlight, reflects a full spectrum of UV/VIS/NIR onto a secondary reflector that transmits VIS/NIR and reflects a uniform flux of UV/VIS onto the sample exposure plane, said sample exposure plane located in the chamber means near said multi-faceted concentrator array to provide concurrent levels of temperature and/or relative humidity that allows sample materials to be subjected to accelerated irradiance exposure factors for a significant period of time of about 3 to 10 days to provide a corresponding time of about at least a years worth of representative weathering of sample materials.

7. The apparatus of claim 1 wherein said multi-faceted concentrator comprises: facets that receive incident natural sunlight, reflects a full spectrum of UV/VIS/NIR onto a secondary reflector that transmits VIS/NIR and reflects a uniform flux of UV/VIS onto the sample exposure plane, said sample exposure plane located in the chamber means that provide concurrent levels of temperature and/or relative humidity that allow sample materials to be subjected to accelerated irradiance exposure factors for a significant period of time of about 3 to 10 days to provide a corresponding time of about at least a years worth of representative weathering of sample materials.

8. An apparatus for providing ultra-accelerated natural sunlight exposure testing for sample materials under controlled weathering conditions comprising: means for concentrating solar flux uniformly as concentrated uniform reflected light, and means for directing said concentrated uniform reflected light, and means for directing said concentrated uniform reflected light onto sample materials contained in a chamber having means to provide single or multiple concurrent levels of temperature and/or relative humidity, wherein said means for concentrating solar flux uniformly and means for directing concentrated uniform reflected light comprising:

a multi-stepped concentrator that receives incident natural sunlight, transmits VIS/NIR and reflects a uniform flux of UV/VIS onto a vertically disposed sample exposure plane disposed in chamber means about a common axis of reflective elements of said multi-stepped concentrator to provide concurrent levels of temperature and/or relative humidity that allow sample materials to be subjected to accelerated irradiance exposure factors for a significant period of time of about 3 to 10 days to provide a corresponding time of about at least a years worth of representative weathering of sample materials.

9. An apparatus for providing ultra-accelerated natural sunlight exposure testing for sample materials under controlled weathering conditions comprising: means for concentrating solar flux uniformly as concentrated uniform refracted light, and means for directing said concentrated uniform refracted light onto sample materials contained in a chamber having means to provide single or multiple concurrent levels of temperature and/or relative humidity at high levels of up to 100× of natural sunlight, wherein said means for concentrating solar flux uniformly and means for directing concentrated uniform refracted light comprising:

a) a front surface VIS/NIR reflective coating means to reflect VIS/NIR and transmit UV/VIS;

b) a Fresnel lens means to receive transmitted UV/VIS and transmit a desired spectral range of uniform concentrated spectrally split natural sunlight; and c) chamber means capable of receiving said desired range of uniform concentrated spectrally split natural sunlight in enclosed single or multiple concurrent levels of temperature and/or relative humidity providing means to allow sample materials to be subjected to accelerated irradiance exposure factors for a significant period of time of about 3 to 10 days to provide a corresponding time of about at least a years worth of representative weathering of sample materials.

10. An apparatus for providing ultra-accelerated natural sunlight exposure testing for sample materials under controlled weathering conditions comprising: means for concentrating solar flux uniformily as concentrated uniform refracted light, and means for directing said concentrated uniform refracted light onto sample materials contained in a chamber having means to provide single or multiple concurrent levels of temperature and/or relative humidity, wherein said means for concentrating solar flux uniformly and means for directing concentrated uniform refracted light comprising:

a) a Fresnel lens having a heat mirror coating on either its top or bottom or both sides to reflect VIS/NIR and transmit UV/VIS; and b) chamber means capable of receiving transmitted UV/VIS in enclosed single or multiple concurrent levels of temperature and/or relative humidity providing means to allow sample materials to be subjected to accelerated-irradiance exposure factors for a significant period of time of about 3 to 10 days to provide a corresponding time of about at least a year's worth of representative weathering of sample materials.

11. An apparatus for providing ultra-accelerated natural sunlight exposure testing for sample materials under controlled weathering conditions comprising: means for concentrating solar flux uniformly as concentrated uniform refracted light, and means for directing said concentrated uniform refracted light onto sample materials contained in a chamber having means to provide single or multiple concurrent levels of temperature and/or relative humidity at high levels of up to 100× of natural sunlight, wherein said means for concentrating solar flux uniformly and means for directing concentrated uniform refracted light onto sample materials comprising:

a) a Fresnel lens that receives incident uniform, non-concentrated natural sunlight and transmits a desired spectral range, a heat mirror means between said Fresnel lens and sample materials that reflects VIS/NIR but transmits UV/VIS; and b) chamber means capable of receiving directed UV/VIS from said heat mirror means that encloses single or multiple concurrent levels of temperature and/or relative humidity providing means to allow sample materials to be subjected to accelerated-irradiance exposure factors for a significant period of time of about 3 to 10 days to provide a corresponding time of about at least a years worth of representative weathering of sample materials.

12. An apparatus for providing ultra-accelerated natural sunlight exposure testing for sample materials under controlled weathering conditions comprising: means for concentrating solar flux uniformly as concentrated uniform refracted light, and means for directing said concentrated uniform refracted light onto sample materials contained in a chamber having means to provide single or multiple concurrent levels of temperature and/or relative humidity, wherein said means for concentrating solar flux uniformly and means for directing concentrated uniform refracted light onto a sample materials comprising:

a) a first Fresnel/prism array that receives incident uniform, non-concentrated natural sunlight and spatially separates same into distinct wavelengths;

b) a second Fresnel/prism array having a masking pattern on its top surface to block unwanted wavelengths $\lambda > \lambda_{cutoff}$ of high VIS and NIR and transmit and recombine UV/VIS into a chamber means; and c) chamber means capable of receiving said recombined ultra-accelerated natural sunlight in enclosed single or multiple concurrent levels of temperature and/or relative humidity providing means to allow sample materials to be subjected to accelerated-irradiance exposure factors for a significant period of time of about 3 to 10 days to provide a corresponding time of about at least a years worth of representative weathering of sample materials.

13. An apparatus for providing ultra-accelerated natural sunlight exposure testing for sample materials under controlled weathering conditions comprising: means for concentrating solar flux uniformly as concentrated uniform refracted light, and means for directing said concentrated uniform refracted light onto sample materials contained in a chamber having means to provide single or multiple concurrent levels of temperature and/or relative humidity, wherein said means for concentrating solar flux uniformly and means for directing concentrated uniform refracted light onto a sample materials comprising:

a) a first prism array to affect spatially/distinct wavelengths from incident uniform, non-concentrated sunlight and provide adjustable stop blocks of light at wavelengths $\lambda > \lambda_{UV/VIS}$ or $\lambda > \lambda_{cutt-off}$;

b) a second prism array to reconstruct or homogenize wavelengths from said first prism array to provide a uniform distribution of spectrally selected light; and c) chamber means capable of receiving said distribution of spectrally selected light in enclosed single or multiple concurrent levels of temperature and/or relative humidity providing means to allow sample materials to be subjected to accelerated-irradiance exposure factors for a significant period of time of about 3 to 10 days to provide a corresponding time of about at least a years worth of representative weathering of sample materials.

14. An apparatus for providing ultra-accelerated natural sunlight exposure testing for sample materials under controlled weathering conditions comprising: means for concentrating solar flux uniformly as concentrated uniform refracted light, and means for directing said concentrated uniform refracted light onto sample materials contained in a chamber having means to provide single or multiple concurrent levels of temperature and/or relative humidity, wherein said means for concentrating solar flux uniformly and means for directing concentrated uniform refracted light onto a sample materials comprises:

a) a holographic means that receive uniform, non-concentrated natural sunlight and spectrally splits said sunlight into VIS/NIR and directs said UV/VIS into a chamber means; and b) chamber means capable of receiving UV/VIS in enclosed single or multiple concurrent levels of temperature and/or relative humidity providing means to allow sample materials to be subjected to accelerated-irradiance exposure factors for a significant period of time of about 3 to 10 days to provide a corresponding time of about at least a years worth of representative weathering of sample materials.

15. An apparatus for providing ultra-accelerated natural sunlight exposure testing for sample materials under controlled weathering conditions comprising: means for concentrating solar flux uniformly as concentrated uniform refracted light, and means for directing said concentrated uniform refracted light onto sample materials contained in a chamber having means to provide single or multiple concurrent levels of temperature and/or relative humidity, wherein said means for concentrating solar flux uniformly and means for directing concentrated uniform refracted light onto sample materials comprises:

a) a holographic device that receives and concentrates incident uniformity, non-concentrated natural sunlight and spectrally splits said sunlight into VIS/NIR and UV/VIS; and b) a secondary concentrator that receives said UV/VIS and directs said UV/VIS into a chamber means; and c) chamber means capable of receiving said UV/VIS in enclosed single or multiple concurrent levels of temperature and/or relative humidity providing means to allow sample materials to be subjected to accelerated-irradiance exposure factors for a significant period of time of about 3 to 10 days to provide a corresponding time of about at least a years worth of representative weathering of sample materials.

16. An apparatus for providing ultra-accelerated natural sunlight exposure testing for sample materials under controlled weathering conditions comprising: means for concentrating solar flux uniformly as concentrated uniform refracted light, and means for directing said concentrated uniform refracted light onto sample materials contained in a chamber having means to provide single or multiple concurrent levels of temperature and/or relative humidity, wherein said means for concentrating solar flux uniformly and means for directing concentrated uniform refracted light onto sample materials comprises:

a) a holographic device that receive incident uniform, non-concentrated natural sunlight and spectrally splits said sunlight into a VIS/NIR fraction and a UV/VIS fraction;

b) a heat mirror that reflects the VIS/NIR fraction and transmits the UV/VIS fraction onto a chamber means; and c) chamber means capable of receiving said UV/VIS fraction from the heat mirrors into enclosed single or multiple concurrent levels of temperature and/or relative humidity providing means to allow sample materials to be subjected to accelerated-irradiance exposure factors for a significant period of time of about 3 to 10 days to provide a corresponding time of about at least a years worth of representative weathering of sample materials.

17. An apparatus for providing ultra-accelerated natural sunlight exposure testing for sample materials under controlled weathering conditions comprising: means for concentrating solar flux uniformly as concentrated uniform refracted light, and means for directing said concentrated uniform refracted light onto sample materials contained in a chamber having means to provide single or multiple concurrent levels of temperature and/or relative humidity, wherein said means for concentrating solar flux uniformly and means for directing concentrated uniform refracted light onto sample materials comprises:

a) a 2-dimensional or 3-dimensional array device of micro lenses that receive uniform, non-concentrated natural sunlight and refractively concentrates and/or spectrally splits said sunlight into VIS/NIR and UV/VIS fractions; and
  b) a surface means to transmit said VIS/NIR and reflect said UV/VIS; and
  c) chamber means capable of receiving refracted UV/VIS into enclosed single or multiple concurrent levels of temperature and/or relative humidity providing means to allow sample materials to be subjected to accelerated-irradiance exposure factors for a significant period of time of about 3 to 10 days to provide a corresponding time of about at least a years worth of representative weathering of sample materials.

18. An apparatus for providing ultra-accelerated natural sunlight exposure testing for sample materials under controlled weathering conditions comprising: means for concentrating solar flux uniformly as concentrated uniform refracted light and means for directing said concentrated uniform refracted light onto sample materials contained in a chamber having means to provide single or multiple concurrent levels of temperature and/or relative humidity, wherein said means for concentrating solar flux uniformly and means for directing concentrated uniform refracted light onto a sample materials comprises:

a) a multi-faceted array of lenses device means that receive incident uniform, non-concentrated natural sunlight;
  b) a heat mirror means that reflects a VIS/NIR fraction of said sunlight and transmits a UV/VIS fraction of said sunlight; and
  c) chamber means capable of receiving said transmitted UV/VIS fraction in enclosed single or multiple concurrent levels of temperature and/or relative humidity providing means to allow sample materials to be subjected to accelerated-irradiance exposure factors for a significant period of time of about 3 to 10 days to provide a corresponding time of about at least a years worth of representative weathering of sample materials.

* * * * *